(12) United States Patent
Kawaguchi

(10) Patent No.: US 6,814,705 B2
(45) Date of Patent: *Nov. 9, 2004

(54) ARTERIOSCLEROSIS-DEGREE EVALUATING APPARATUS

(75) Inventor: Keizoh Kawaguchi, Komaki (JP)

(73) Assignee: Colin Medical Technology Corporation, Komaki (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/440,182

(22) Filed: May 19, 2003

(65) Prior Publication Data

US 2004/0064055 A1 Apr. 1, 2004

(30) Foreign Application Priority Data

Sep. 27, 2002 (JP) ........................... 2002-283076

(51) Int. Cl.[7] ................................. A61B 5/00
(52) U.S. Cl. ................. 600/500; 600/485; 600/490
(58) Field of Search ......................... 600/485, 450, 600/493, 494–495, 496, 500, 502–503

(56) References Cited

U.S. PATENT DOCUMENTS 6,612,993 B2 * 9/2003 Narimatsu ................. 600/500
6,659,958 B2 * 12/2003 Narimatsu et al. ......... 600/485
6,702,754 B2 * 3/2004 Ogura et al. ............... 600/500

FOREIGN PATENT DOCUMENTS

| EP | 1 159 914 A2 | 12/2001 |
| JP | A 2000-254104 | 9/2000 |
| JP | A-2001-190506 | 7/2001 |
| WO | WO 02/05726 A2 | 1/2002 |

OTHER PUBLICATIONS

Delgado–Almeida et al., "Suprasystolic Arterial Pulse Waveform Analysis: New hemodynamic parameter for hypertension," American Journal of Hypertension, vol. 15, No. 4, Part 2, pp. 73A, Apr. 2002.

Wang et al., "Reduction of cardiac functional reserve and elevation of aortic stiffness in hyerlipidemic Yucatan minipigs with systemic and coronary atherosclerosis," Vascular Pharmacolosy, vol.39, No. ½, pp. 69–76, XP009012194, Jul. 2002.

* cited by examiner

Primary Examiner—Robert L. Nasser
(74) Attorney, Agent, or Firm—Oliff & Berridge, PLC

(57) ABSTRACT

An apparatus for evaluating a degree of arteriosclerosis of a living subject, including: a pulse-wave detecting device adapted to be worn on a first portion of the living subject; a pressing device adapted to be worn on a second portion of the subject located on a distal side of the first portion, for pressing the second portion so as to restrict a flow of blood at the second portion; and an arteriosclerosis-related information obtaining device which obtains arteriosclerosis-related information used for evaluating said degree of arteriosclerosis of the subject, based on a peak point of an incident-wave component, and a peak point of a reflected-wave component, of a pulse of a pulse wave that is detected by the pulse-wave detecting device in a state in which the flow of blood is restricted by the pressing device.

12 Claims, 5 Drawing Sheets

ARTERIOSCLEROSIS-DEGREE EVALUATING APPARATUS

BACKGROUND OF THE INVENTION

1. Field of the Invention

The present invention relates to an arteriosclerosis-degree evaluating apparatus for evaluating a degree of arteriosclerosis of a living subject.

2. Related Art Statement

As examples of a method of evaluating a degree of arteriosclerosis of a living subject, there are known an ultrasonic echo method in which the degree of arteriosclerosis is evaluated directly from an image of a blood vessel of the subject taken using an ultrasonic wave, and a method in which the degree of arteriosclerosis is evaluated indirectly from a measured pulse-wave propagation velocity PWV at which a pulse wave propagates in the subject.

In general, the pulse-wave propagation velocity PWV is measured in the following manner: Two sensors are worn on two body portions of the subject for detecting heartbeat-synchronous signals respectively from the two body portions. A pulse-wave propagation time DT is determined as a time difference between a time of detection of a prescribed portion of one of the two heartbeat-synchronous signals and a time of detection of a corresponding prescribed portion of the other of the two heartbeat-synchronous signals. Further, a pulse-wave propagation distance is determined as a distance between the two body portions on which the two sensors are respectively worn. The pulse-wave propagation velocity PWV is obtained by dividing the pulse-wave propagation distance by the pulse-wave propagation time DT. JP-A-2001-190506 discloses one example of an arteriosclerosis-degree evaluating apparatus wherein a pulse-wave propagation velocity PWV is determined for evaluating a degree of arteriosclerosis. Described in detail, the disclosed apparatus comprises a heart-sound microphone adapted to be worn on a chest of a living subject and a pressure pulse wave sensor adapted to be worn on a neck portion of the subject. In the disclosed apparatus, the pulse-wave propagation velocity PWV is determined based on a time difference between a time of detection of a start point of a second heart sound II and a time of detection of a notch point of a heartbeat-synchronous pulse of a pulse wave detected from a carotid artery, and a prescribed distance between the two body portions on which the heart-sound microphone and the pressure pulse wave sensor are respectively worn.

Since arteriosclerosis induces various kinds of diseases such as cerebrovascular disease and coronary disease, it is desirable that degree of arteriosclerosis be evaluated daily. However, an ultrasonic diagnosing apparatus used in the ultrasonic echo method is very expensive. For obtaining a pulse-wave propagation velocity, two sensors for respectively detecting two heartbeat-synchronous signals need to be appropriately worn on respective two body portions, for detecting pulses each having an accurate waveform with substantially no noise. Thus, the pulse-wave propagation velocity cannot be easily measured, and a certain degree of skill is needed to measure the velocity.

SUMMARY OF THE INVENTION

It is therefore an object of the present invention to provide an arteriosclerosis-degree evaluating apparatus capable of easily evaluating a degree of arteriosclerosis of a living subject.

The above-indicated object of the present invention has been achieved by the present invention. According to the present invention, there is provided an apparatus for evaluating a degree of arteriosclerosis of a living subject, comprising: a pulse-wave detecting device adapted to be worn on a first portion of the living subject; a pressing device adapted to be worn on a second portion of the subject located on a distal side of the first portion, for pressing the second portion so as to restrict a flow of blood at the second portion; and an arteriosclerosis-related information obtaining means for obtaining arteriosclerosis-related information used for evaluating the degree of arteriosclerosis of the subject, based on a peak point of an incident-wave component, and a peak point of a reflected-wave component, of a pulse of a pulse wave that is detected by the pulse-wave detecting device in a state in which the flow of blood is restricted by the pressing device.

In the present arteriosclerosis-degree evaluating apparatus, when the flow of blood is restricted by the pressing device at the second portion of the subject on which the pressing device is worn, a reflected wave is generated at that second portion. Accordingly, the pulse wave detected by the pulse-wave detecting device worn on the first portion of the subject that is located on the proximal side of the pressing device is a composite wave consisting of an incident wave that represents an increase of a pressure in the artery that is caused by ejection of blood from the left ventricle of the heart of the subject, and the reflected wave generated at the second portion on which the pressing device is worn. The magnitude and the velocity of the reflected wave increase with an increase of the hardness of the artery. Accordingly, the location and the magnitude of a peak point of the reflected-wave component of the pulse vary relative to those of a peak point of the incident-wave component of the pulse, depending upon the degree of arteriosclerosis. Therefore, the present apparatus is capable of evaluating the degree of arteriosclerosis of the subject, based on the arteriosclerosis-related information that is obtained, by the arteriosclerosis-related information obtaining means, on the basis of the respective peak points of the incident-wave component, and the reflected-wave component, of the pulse. In the present apparatus, the single pulse-wave detecting device and the single pressing device are worn on the subject for evaluating the degree of arteriosclerosis of the subject, without using an expensive apparatus. Further, the present apparatus is capable of evaluating the degree of arteriosclerosis more easily than the conventional arrangement wherein the two detecting devices for respectively detecting the two heartbeat-synchronous signals are worn on the respective two body portions of the subject.

The arteriosclerosis-related information obtaining means preferably obtains, as the arteriosclerosis-related information, at least one of: (a) a time difference between a time of occurrence of the peak point of the incident-wave component of the pulse and a time of occurrence of the peak point of the reflected-wave component of the pulse; (b) a difference between a magnitude of the pulse at the time of occurrence of the peak point of the incident-wave component thereof and a magnitude of the pulse at the time of occurrence of the peak point of the reflected-wave component thereof; (c) a ratio between a magnitude of the pulse at the time of occurrence of the peak point of the reflected-wave component thereof, and a magnitude of the pulse at the time of occurrence of the peak point of the incident-wave component thereof; (d) a ratio of the difference between the magnitude of the pulse at the time of occurrence of the peak point of the incident-wave component thereof and the magnitude of the pulse at the time of occurrence of the peak point of the reflected-wave component thereof, to a pulse pressure of the pulse, and (e) a ratio of the ratio between the magnitude of the pulse at the time of occurrence of the peak point of the incident-wave component thereof and the magnitude of the pulse at the time of occurrence of the peak point of the reflected-wave component thereof, to the pulse pressure of the pulse.

In one preferred form of the present invention, the pulse-wave detecting device comprises a pressing bag adapted to be wound around the first portion of the subject, and the apparatus further comprises: a pressure changing means for changing a pressure in the pressing bag; and a blood-pressure determining means for determining a blood pressure value of the subject based on a signal which is obtained from the pressing bag when the pressure in the pressing bag is changed by the pressure changing means. According to this arrangement, the apparatus obtains, in addition to the arteriosclerosis-related information, the blood pressure value based on the signal obtained from the pressing bag.

In another preferred form of the present invention, the pulse-wave detecting device comprises a first pressing bag adapted to be wound around the first portion of the subject, and the pressing device comprises a second pressing bag adapted to be worn on the second portion of the subject, the first and second pressing bags being connected integrally to each other by a connecting member such that the first and second pressing bags are spaced apart from each other. According to this arrangement, the pulse-wave detecting device and the pressing device can be easily worn on the respective first and second portions of the subject.

In a preferred mode of the above-indicated form of the invention, the apparatus further comprises: a first pressure changing means for changing a pressure in the first pressing bag; and a blood-pressure determining means for determining a blood pressure value of the subject based on a signal which is obtained from the first pressing bag when the pressure in the first pressing bag is changed by the pressure changing means. According to this arrangement, the apparatus obtains, in addition to the arteriosclerosis-related information, the blood pressure value based on the signal obtained from the first pressing bag.

BRIEF DESCRIPTION OF THE DRAWINGS

The above and optional objects, features, and advantages of the present invention will be better understood by reading the following detailed description of preferred embodiments of the invention when considered in conjunction with the accompanying drawings, in which.

DETAILED DESCRIPTION OF PREFERRED EMBODIMENTS

Hereinafter, there will be described in detail one embodiment of the present invention, by reference to the drawings.

Figure 1:
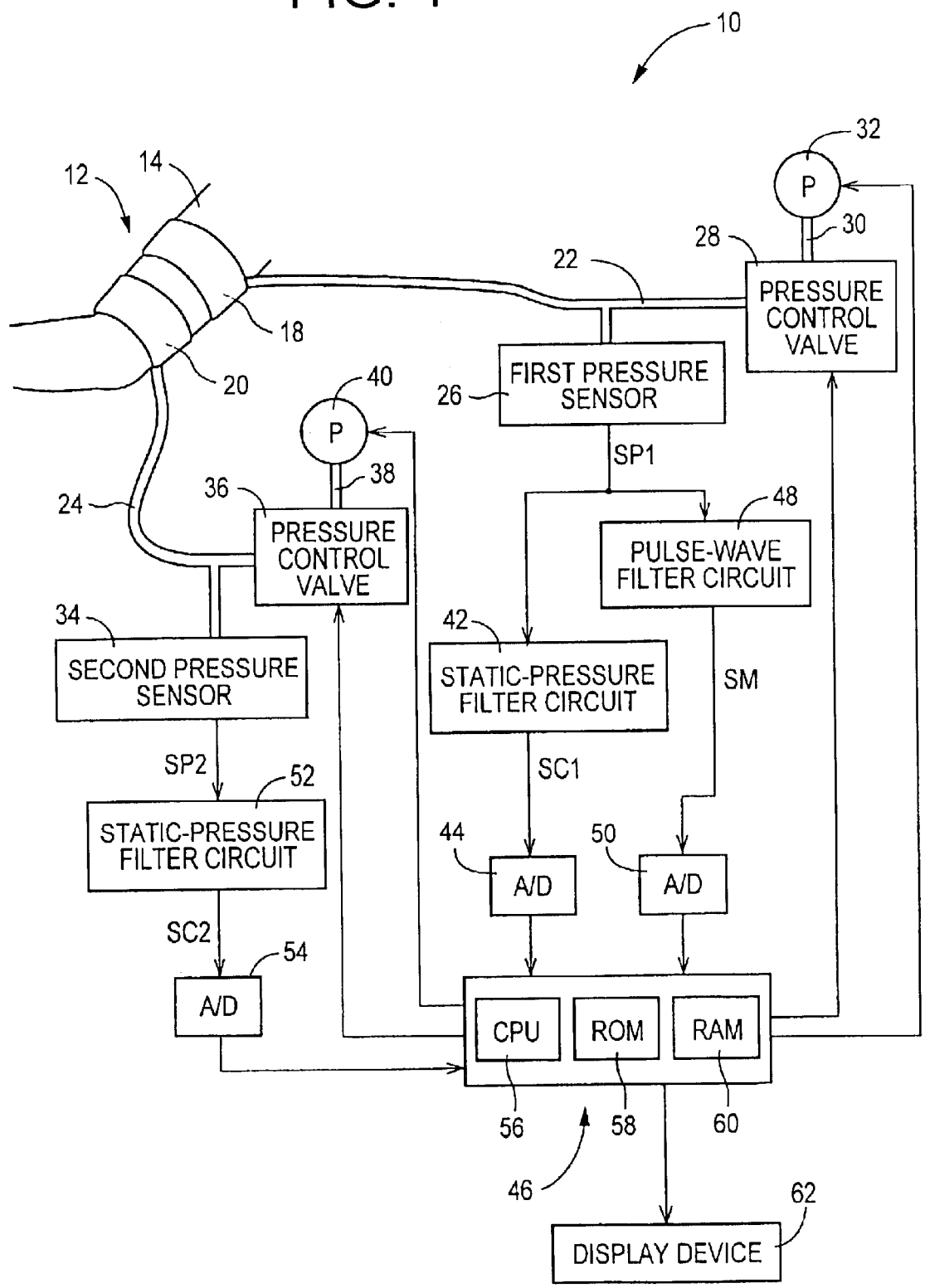
FIG. 1 is a diagrammatic view showing a circuitry of an arteriosclerosis-degree evaluating apparatus to which the present invention is applied.

FIG. 1 is a diagrammatic view showing a circuitry of an arteriosclerosis-degree evaluating apparatus 10 to which the present invention is applied.

Figure 2:
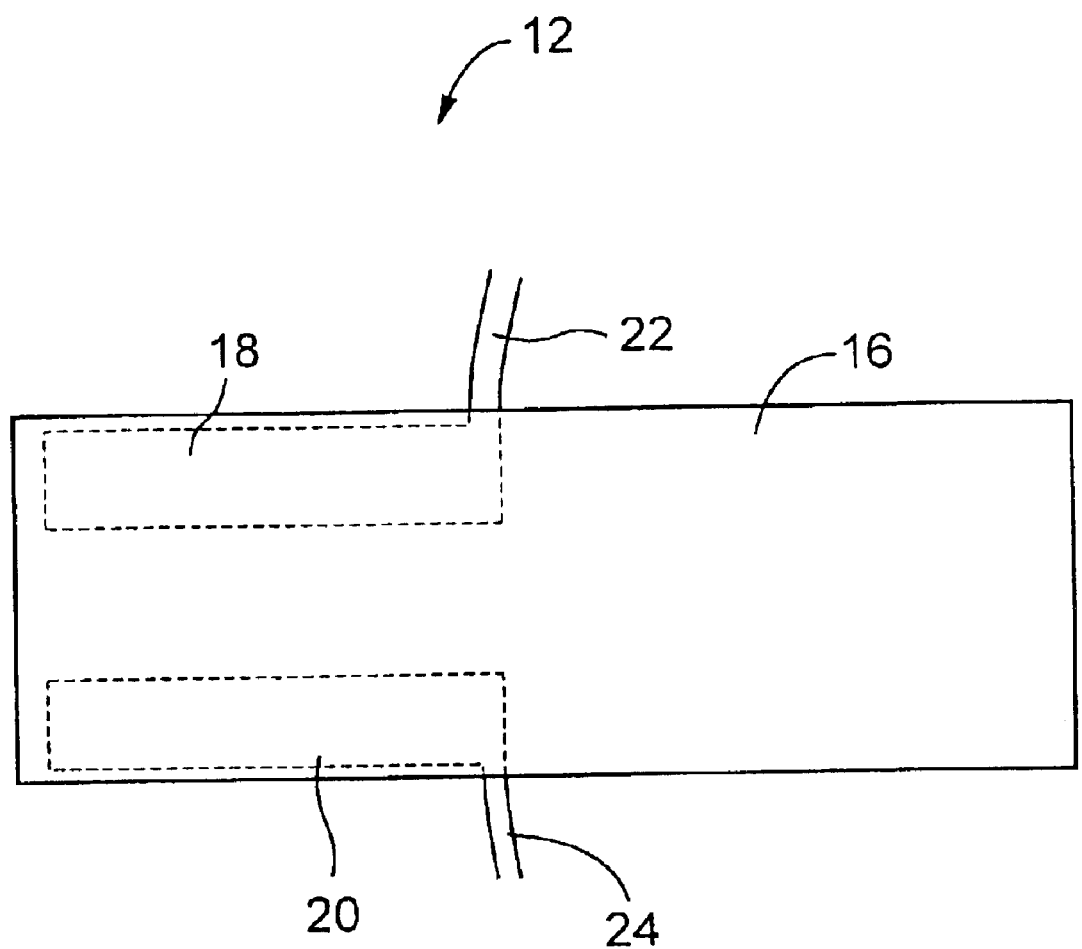
FIG. 2 is an exploded view of a cuff shown in FIG. 1.

As shown in FIG. 1, the present arteriosclerosis-degree evaluating apparatus 10 includes a cuff 12 adapted to be worn around an upper arm 14 of a living subject. In the present apparatus 10, only the cuff 12 is worn on the subject. As shown in the exploded view of FIG. 2, the cuff 12 includes a belt-like bag 16 formed of a cloth which is non-stretchable and has a considerably high degree of rigidity.

In the belt-like bag 16, there are accommodated a first pressing bag 18 functioning as a pulse-wave detecting device, and a second pressing bag 20 functioning as a pressing device, such that, when the cuff 12 is wound around the upper arm 14 of the subject, the first pressing bag 18 is located at a proximal end of the cuff 12 while the second pressing bag 20 is located at a distal end of the cuff 12. Accordingly, when the cuff 12 is wound around the upper arm 14, the first pressing bag 18 is worn on a first portion of the upper arm 14, and the second pressing bag 20 is worn on a second portion of the upper arm 14 that is downstream of the first portion in a direction in which the blood flows in a brachial artery (not shown) of the subject. The belt-like cloth bag 16 functions as a connecting member that connects the first and second pressing bags 18, 20 to each other. Each of the first and second pressing bags 18, 20 is formed of a rubber, and has a longitudinal dimension (e.g., 24 cm) that is substantially equal to a circumferential length of the upper arm 14. To the first and second pressing bags 18, 20, there are connected pipes 22, 24, respectively.

Referring back to FIG. 1, the first pressing bag 18 is connected via the pipe 22 to a first pressure sensor 26 and a pressure control valve 28. The pressure control valve 28 is connected via a pipe 30 to an air pump 32. The second pressing bag 20 is connected via the pipe 24 to a second pressure sensor 34 and a pressure control valve 36. The pressure control valve 36 is connected via a pipe 38 to an air pump 40.

The pressure control valves 28, 36 adjust respective pressures of pressurized air supplied from the air pumps 32, 40, and supply the pressure-adjusted air to the respective pressing bags 18, 20, or discharge the pressurized air from the respective pressing bags 18, 20, so as to control respective air pressures in the pressing bags 18, 20.

The first pressure sensor 26 detects the air pressure in the first pressing bag 18, and supplies a first pressure signal SP1 representing the detected air pressure, to a static-pressure filter circuit 42 and a pulse-wave filter circuit 44. The static-pressure filter circuit 42 has a low-pass filter and extracts, from the first pressure signal SP1, a first pressing-pressure signal SC1 representing a static-pressure component contained in the signal SP1, i.e., a pressing pressure of the first pressing bag 18 (hereinafter referred to as "first pressing pressure PC1"). The first pressing-pressure signal SC1 is supplied to an electronic control device 46 which will be described later, via an analog-to-digital (A/D) converter 44.

The pulse-wave filter circuit 48 includes a band-pass filter which transmits a frequency component of the first pressure signal SP1 that has frequencies in a range of about 1 to 30 Hz, and extracts, from the signal SP1, a pulse-wave signal SM as an oscillatory component of the signal SP1. The pulse-wave signal SM is supplied to the control device 46 via an A/D converter 50. The pulse-wave signal SM represents a brachial pulse wave which is produced from the brachial artery of the subject and is transmitted to the first pressing bag 18. The brachial pulse wave includes at least one heartbeat-synchronous pulse which is produced from the brachial artery in synchronism with at least one heartbeat of the subject.

The second pressure sensor 34 detects the air pressure in the second pressing bag 20, and supplies a second pressure signal SP2 representing the detected air pressure, to a static-pressure filter circuit 52. The static-pressure filter circuit 52 is similar in construction to the static-pressure filter circuit 42 connected to the first pressure sensor 26. The static-pressure filter circuit 52 extracts, from the second pressure signal SP2, a second pressing-pressure signal SC2 representing a static-pressure component contained in the signal SP2, i.e., a pressing pressure of the second pressing bag 20 (hereinafter referred to as "second pressing pressure PC2"). The second pressing-pressure signal SC2 is supplied to the electronic control device 46 via an A/D converter 54.

The electronic control device 46 is essentially provided by a so-called microcomputer including a CPU (central processing unit) 56, a ROM (read only memory) 58, a RAM (random access memory) 60, an input-and-output (I/O) port, not shown, etc, and the CPU 56 processes signals according to control programs pre-stored in the ROM 58, while utilizing a temporary-storage function of the RAM 60. The CPU 56 outputs, from the I/O port, drive signals to the two air pumps 32, 40 and the two pressure control valves 28, 36, so as to control the respective operations thereof and thereby control the first pressing pressure PC1 and the second pressing pressure PC2. In addition, the CPU 56 implements the control functions shown in FIG. 3, which will be described later in greater detail, so as to determine a blood pressure value BP, and obtain arteriosclerosis-related information, of the subject. Further, the CPU 56 controls a display device 62 to display the determined blood pressure value BP and the obtained arteriosclerosis-related information.

Figure 3:
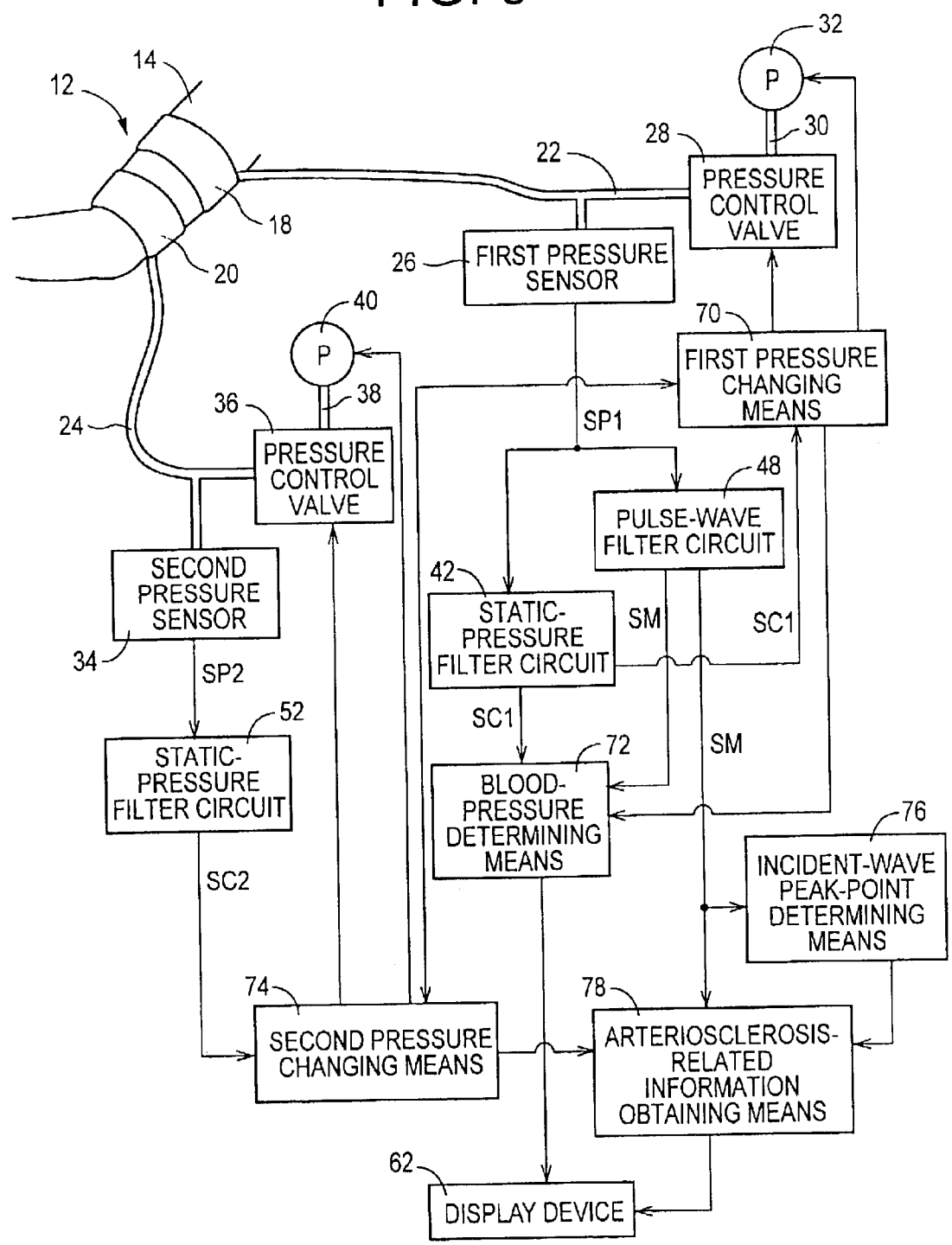
FIG. 3 is a block diagram for explaining essential control functions of a CPU (central processing unit) of the apparatus of FIG. 1.

FIG. 3 is a block diagram for explaining essential control functions of the CPU 56 of the present arteriosclerosis-degree evaluating apparatus 10.

A first pressure changing means or device 70 operates the pressure control valve 28 and the air pump 32 to carry out a blood-pressure-measurement-related operation and a pulse-wave-detecting-pressure-related operation, described below. In the blood-pressure-measurement-related operation, the first pressing pressure PC1 is quickly increased to a pre-set target pressure PM1 (e.g., 180 mmHg) that would be higher than a systolic blood pressure $BP_{SYS}$ of the upper arm 14 of the subject. Subsequently, the first pressing pressure PC1 is slowly decreased at a pre-set rate of, e.g., 2 or 3 mmHg/sec until a blood-pressure determining means or device 72, described below, determines a blood pressure value BP of the subject. After the blood pressure value BP of the subject has been determined by the blood-pressure determining means 72, the first pressing pressure PC1 is released to an atmospheric pressure. The pulse-wave-detecting-pressure-related operation is carried out a prescribed recovery time "Tr" after the blood-pressure-measurement-related operation conducted by the first pressure changing means 70. In the pulse-wave-detecting-pressure-related operation, the first pressure changing means 70 controls the first pressing pressure PC1 to a pulse-wave detecting pressure PM2, and maintains the first pressing pressure PC1 at the pulse-wave detecting pressure PM2 for a time period corresponding to at least one heartbeat, with the second pressing pressure PC2 being maintained at a blood-flow stopping pressure by a second pressure changing means or device 74. The second pressure changing means 74 and the blood-flow stopping pressure will be described later in greater detail.

The above-described recovery time Tr is a time period needed for the tissue of the subject which has changed due to the pressing of the first pressing bag 18 during the blood-pressure-measurement-related operation, to recover to its normal state prior to the pressing. The recovery time Tr is pre-set at about several tens of seconds, for instance. The above-described pulse-wave detecting pressure PM2 is pre-set at a value that falls within a range between a diastolic blood pressure $BP_{DIA}$ and a mean blood pressure $BP_{MEAN}$, of the subject. For instance, the pulse-wave detecting pressure PM2 is pre-set at an average value of the diastolic blood pressure $BP_{DIA}$ and the mean blood pressure $BP_{MEAN}$. The reason for pre-setting the pulse-wave detecting pressure PM2 to the above-described level is as follows: If the pulse-wave detecting pressure PM2 is higher than the mean blood pressure $BP_{MEAN}$, the pulse wave extracted by the pulse-wave filter circuit 48 is deformed. On the other hand, if the pulse-wave detecting pressure PM2 is too low, the pulse wave does not have a sufficiently great magnitude, and a peak point of a pulse of the pulse wave becomes unclear.

The blood-pressure determining means 72 determines, according to a well-known oscillometric method, a systolic blood pressure value $BP_{SYS}$, a mean blood pressure value $BP_{MEAN}$, and a diastolic blood pressure value $BP_{DIA}$, of the upper arm 14 of the subject, based on the variation of respective amplitudes of pulses of the brachial pulse wave represented by the pulse-wave signal SM continuously supplied from the pulse-wave filter circuit 48, and the first pressing-pressure signal SC1 continuously supplied from the static-pressure filter circuit 42, during the slow decreasing of the first pressing pressure PC1 under the control of the first pressure changing means 70. The thus determined blood pressure values $BP_{SYS}$, $BP_{MEAN}$, $BP_{DIA}$ are displayed by the display device 62.

After the first pressing pressure PC1 has been kept, for the time period corresponding to at least one heartbeat, at the pulse-wave detecting pressure PM2 by the first pressure changing means 70, the second pressure changing means 74 operates the pressure control valve 36 and the air pump 40, so as to control the second pressing pressure PC2 to the prescribed blood-flow stopping pressure at which the flow of blood is stopped at the second portion of the upper arm 14 on which the second pressing bag 20 is worn. For instance, the blood-flow stopping pressure is pre-set at a value equal to the above-described target pressure PM1, i.e., 180 mmHg.

An incident-wave peak-point determining means or device 76 identifies a peak point of a pulse of the brachial pulse wave represented by the pulse-wave signal SM which is supplied from the pulse-wave filter circuit 48 when the first pressing pressure PC1 is kept at the pulse-wave detecting pressure PM2 by the first pressure changing means 70 and the second pressing pressure PC2 is not kept at the blood-flow stopping pressure by the second pressure changing means 74, and determines a time of occurrence of the identified peak point as a time of occurrence of a peak point of an incident-wave component of the pulse. The incident-wave component of the pulse of the brachial pulse wave indicates a pressure increase in the artery resulting from ejection of blood from the left ventricle of the heart of the subject. The brachial pulse wave is a composite wave consisting of the incident-wave component and a reflected-wave component that is generated by reflection of the incident-wave component at a peripheral portion of the artery.

An arteriosclerosis-related information obtaining means or device 78 initially determines a time of occurrence of a peak point of an incident-wave component, and a time of occurrence of a peak point of a reflected-wave component, of a pulse of the brachial pulse wave represented by the pulse-wave signal SM which is continuously supplied from the pulse-wave filter circuit 48 when the first pressing pressure PC1 is kept at the pulse-wave detecting pressure PM2 by the first pressure changing means 70 and the second pressing pressure PC2 is kept at the blood-flow stopping pressure by the second pressure changing means 74. This brachial pulse wave detected when the second pressing pressure PC2 is kept at the blood-flow stopping pressure is hereinafter referred to as "blood-flow-stop brachial pulse wave".

When the flow of blood is stopped at the second portion of the upper arm 14 of the subject by the second pressing bag 20, the incident wave is entirely reflected at the second portion on which the second pressing bag 20 is worn. In this case, the magnitude of the reflected-wave component becomes large, and the peak point of the reflected-wave component defines a peak point of a pulse of the brachial pulse wave detected when the blood flow is stopped at the second portion. Accordingly, the arteriosclerosis-related information obtaining means 78 determines, as the peak point of the reflected-wave component of the pulse of the blood-flow-stop brachial wave, the peak point of the pulse of the blood-flow-stop brachial pulse wave. In the meantime, the peak point of the incident-wave component of the pulse of the blood-flow-stop brachial pulse wave is more or less unclear, as compared with that of the brachial pulse wave detected when the flow of blood is not stopped by the second pressing bag 20. It is, however, noted that the incident-wave component is not influenced by the state of the artery on the distal side of the first portion on which the first pressing bag 18 is worn. Accordingly, the arteriosclerosis-related information obtaining means 78 superposes the pulse of the brachial pulse wave used by the incident-wave peak-point determining means 76 for determining the peak point of the incident-wave component, and the pulse of the blood-flow-stop brachial pulse wave, on each other, such that prescribed reference points (e.g., rising points) of the respective two pulses coincide with each other. Subsequently, the arteriosclerosis-related information obtaining device 78 determines, as a time of occurrence of the peak point of the incident-wave component of the blood-flow-stop brachial pulse wave, the time of occurrence of the peak point of the incident-wave component determined by the incident-wave peak-point determining means 76.

The arteriosclerosis-related information obtaining means 78 further calculates a time difference ΔT between the times of occurrence of the respective peak points of the incident-wave and reflected-wave components of the pulse of the blood-flow-stop brachial pulse wave determined as described above, and a ratio R between a magnitude of the pulse at the time of occurrence of the peak point of the incident-wave component thereof, and that of the pulse at the time of occurrence of the peak point of the reflected-wave component thereof. This ratio R is hereinafter referred to as "magnitude ratio R". The determined time difference ΔT and the magnitude ratio R are displayed by the display device 62. Each of the time difference ΔT and the magnitude ratio R is arteriosclerosis-related information. As arteriosclerosis advances, the velocity of the reflected wave increases. Accordingly, the above-indicated time difference ΔT decreases as arteriosclerosis advances. The magnitude ratio R is expressed by a fractional expression whose denominator may be either of the magnitude "a" of the pulse at the time of occurrence of the peak point of the incident-wave component and the magnitude "b" of the pulse at the time of occurrence of the peak point of the reflected-wave component. Where the magnitude ratio R is obtained as a fractional expression represented by R=b/a, the magnitude ratio R increases with an increase of the degree of arteriosclerosis, since the magnitude b of the reflected-wave component increases as arteriosclerosis advances.

Figure 4:
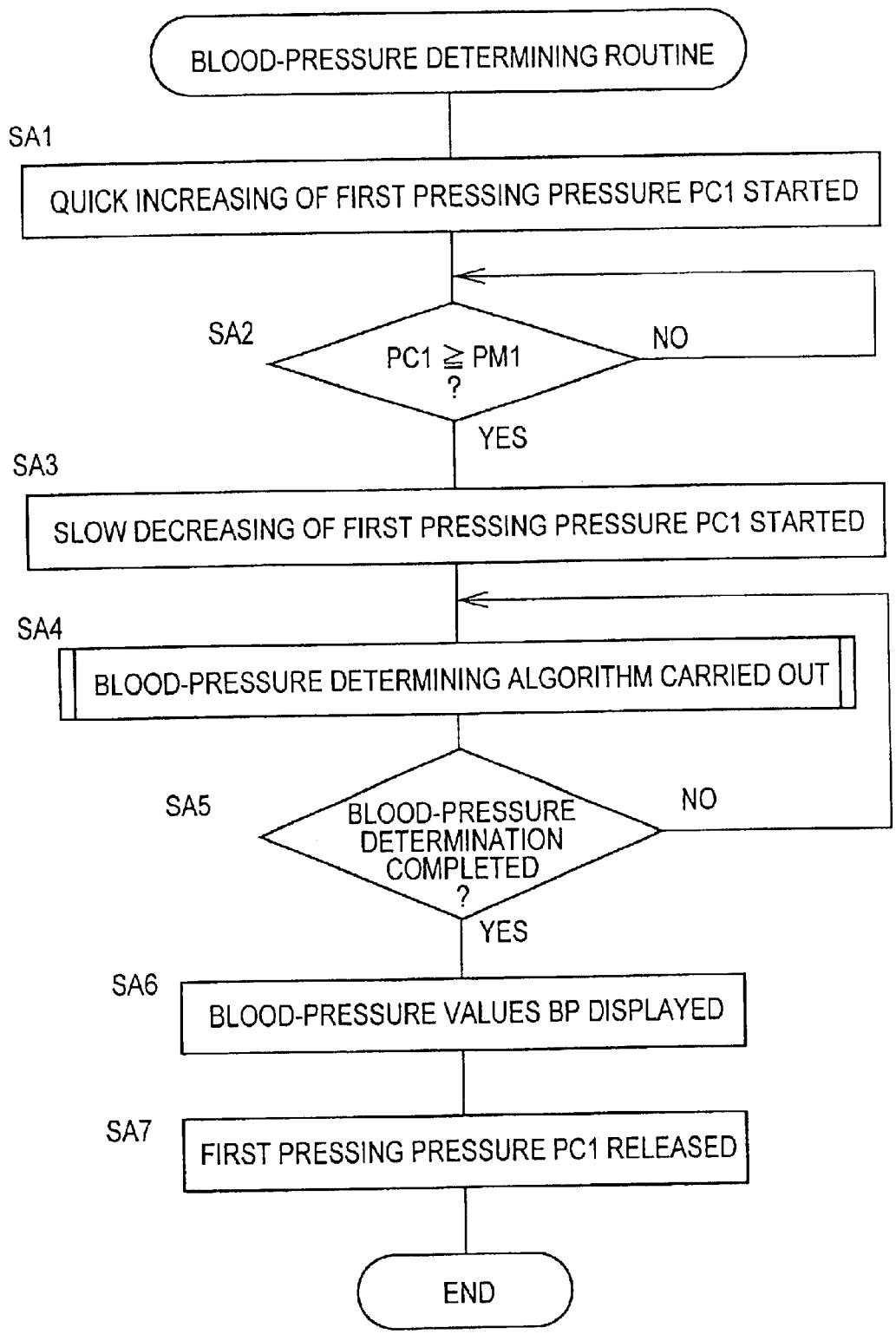
FIG. 4 is a flow chart for explaining a portion of the control functions of the CPU, shown in the block diagram of FIG. 3, the flow chart representing a blood-pressure determining routine.
Figure 5:
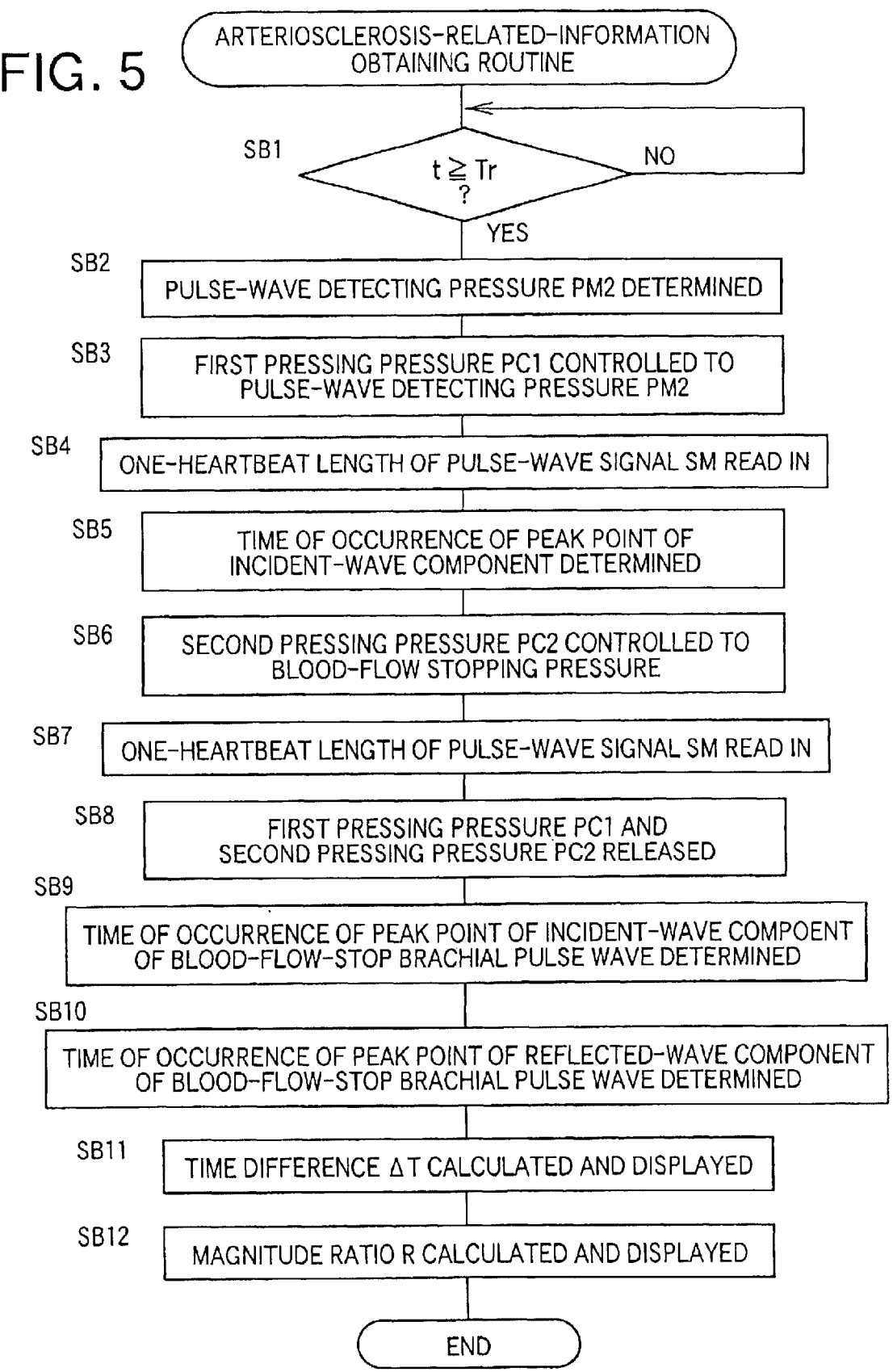
FIG. 5 is a flow chart for explaining another portion of the control functions of the CPU, shown in the block diagram of FIG. 3, the flow chart representing an arteriosclerosis-related-information obtaining routine.

FIGS. 4 and 5 show flow charts for explaining essential control functions of the CPU 56, shown in the block diagram of FIG. 3. The flow chart of FIG. 4 is a blood-pressure determining routine, and the flow chart of FIG. 5 is an arteriosclerosis-related-information obtaining routine.

The control of the CPU 56 begins with Step SA1 (hereinafter, "Step" is omitted, if appropriate) to drive the air pump 32 and operate the pressure control valve 28, so as to start quick increasing of the first pressing pressure PC1. SA1 is followed by SA2 to judge whether the first pressing pressure PC1 is equal to or higher than a pre-set target pressure value PM1 (i.e., 180 mmHg). The CPU 56 repeats this step and continues quick increasing of the first pressing pressure PC1 till a positive or affirmative judgment is made at SA2. In the meantime, if an affirmative judgment is made at SA2, the control of the CPU 56 goes to SA3 to stop the air pump 32 and operate the pressure control valve 28, so as to slowly decrease the first pressing pressure PC1 at a rate of about 3 mmHg/sec.

Subsequently, the CPU 56 carries out SA4 through SA6 corresponding to the blood-pressure determining means 72. At SA4, the CPU 56 determines a systolic blood pressure value $BP_{SYS}$, a mean blood pressure value $BP_{MEAN}$, and a diastolic blood pressure value $BP_{DIA}$ of the subject, according to a known oscillometric BP determining algorithm, based on the variation of respective amplitudes of successive heartbeat-synchronous pulses of the brachial pulse wave represented by the pulse-wave signal SM continuously obtained during the slow decreasing of the first pressing pressure PC1, and respective values of the first pressing pressure PC1 at the respective times of occurrence of those amplitudes. The control flow then goes to SA5 at which the CPU 56 judges whether the determination of blood pressure values BP at SA4 has been completed. SA4 and SA5 are repeated to continue the blood-pressure determining algorithm till an affirmative judgment is made at SA5.

In the meantime, if an affirmative judgment is made at SA5, the CPU 56 carries out SA6 to operate the display device 62 to display the blood pressure values $BP_{SYS}$, $BP_{MEAN}$, and $BP_{DIA}$ determined by repetition of SA4 and SA5. Subsequently, at SA7, the CPU 56 operates the pressure control valve 28 so as to release the first pressing pressure PC1 to an atmospheric pressure. In the flow chart of FIG. 4, SA1 through SA3, and SA7 correspond to the blood-pressure-measurement-related operation carried out by the first pressure changing means 70.

After the blood-pressure determining routine of FIG. 4 has been completed, the CPU 56 carries out the arteriosclerosis-related-information obtaining routine of FIG. 5. The control of the CPU 56 starts with SB1 to judge whether a time duration t that has elapsed since the blood-pressure determining routine of FIG. 4 was completed has exceeded the recovery time Tr pre-set at about several tens of seconds. The CPU 56 repeats this step till an affirmative judgment is made at SB1. In the meantime, if an affirmative judgment is made at SB1, the CPU 56 carries out SB2 to calculate an average value of the mean blood pressure $BP_{MEAN}$ and the diastolic blood pressure $BP_{DIA}$ determined at SA4 of the flow chart of FIG. 4. The CPU 56 determines, as a pulse-wave detecting pressure PM2, the calculated average value.

Subsequently, at SB3, the CPU 56 again drives the air pump 32 and operates the pressure control valve 28, so as to control the first pressing pressure PC1 to the pulse-wave detecting pressure PM2 determined at SB2. Then, the CPU 56 carries out SB4 to read in a one-heartbeat length of the pulse-wave signal SM supplied from the pulse-wave filter circuit 48, with the first pressing pressure PC1 being kept at the pulse-wave detecting pressure PM2.

Subsequently, the CPU 56 carries out SB5 corresponding to the incident-wave peak-point determining means 76. At SB5, the CPU 56 determines a time of occurrence of a peak point of a pulse of the brachial pulse wave that is represented by the one-heartbeat length of the pulse-wave signal SM read in at SB4, as a time of occurrence of a peak point of an incident-wave component of the pulse of the brachial pulse wave.

Subsequently, at SB6, the CPU 56 drives the air pump 40 and operates the pressure control valve 36, so as to control the second pressing pressure PC2 to the blood-flow stopping pressure pre-set at 180 mmHg. When the second pressing pressure PC2 becomes equal to the blood-flow stopping pressure, the CPU 56 implements SB7 to read in a one-heartbeat length of the brachial pulse wave represented by the pulse-wave signal SM supplied from the pulse-wave filter circuit 48, with the second pressing pressure PC2 being kept at the blood-flow stopping pressure. Namely, the CPU 56 reads in a one-heartbeat length of the blood-flow-stop brachial pulse wave.

The control then goes to SB8 at which the CPU 56 stops the two air pumps 32, 40 and operates the two pressure control valves 28, 36, so as to release the first pressing pressure PC1 and the second pressing pressure PC2 to an atmospheric pressure. In the flow chart of FIG. 5, SB1 through SB3, and SB8 correspond to the pulse-wave-detecting-pressure-related operation carried out by the first pressure changing means. 70, and SB6 and SB8 correspond to the second pressure changing means 74.

Subsequently, the CPU 56 implements SB9 through SB12 corresponding to the arteriosclerosis-related information obtaining means 78. At SB9, the CPU 56 first superposes the pulse of the blood-flow-stop brachial pulse wave read in at SB7, and the pulse of the brachial pulse wave read in, at SB4, with the second portion of the upper arm 14 on which the second pressing bag 20 is worn being not pressed by the second pressing bag 20. Described in detail, the pulse of the blood-flow-stop brachial pulse wave read in at SB7 and the pulse of the brachial pulse wave read in at SB4 are superposed on each other, such that respective rising points of the two pulses coincide with each other. Then, the CPU 56 determines, as a time of occurrence of a peak point of an incident-wave component of the pulse of the blood-flow-stop brachial pulse wave, the time of occurrence of the peak point of the incident-wave component of the pulse of the brachial pulse wave determined at SB5. The brachial pulse wave was detected with the second portion of the upper arm 14 being not pressed by the second pressing bag 20.

Subsequently, at SB10, the CPU 56 determines a peak point of the blood-flow-stop brachial pulse wave read in at SB7. Then, the CPU 56 determines, as a time of occurrence of a peak point of a reflected-wave component of the blood-flow-stop brachial pulse wave, the time of occurrence of the determined peak point of the blood-flow-stop brachial pulse wave. The control goes to SB11 at which the CPU 56 calculates a time difference $\Delta T$ between the time of occurrence of the peak point of the incident-wave component determined at SB9 and the time of occurrence of the reflected-wave component determined at SB10. The determined time difference $\Delta T$ is displayed by the display device 62.

Subsequently, at SB12, the CPU 56 calculates a magnitude ratio R of a magnitude "b" of the pulse of the blood-flow-stop brachial pulse wave at the time of occurrence of the peak point of the reflected-wave component thereof determined at SB10, to a magnitude "a" of the pulse of the blood-flow-stop brachial pulse wave at the time of occurrence of the peak point of the incident-wave component determined at SB9. Namely, the magnitude ratio R is obtained by dividing the magnitude b by the magnitude a. The calculated magnitude ratio R is displayed by the display device 62.

In the present arteriosclerosis-related information obtaining apparatus 10, when the flow of blood is stopped by the second pressing bag 20 at the second portion of the upper arm 14 on which the second pressing bag 20 is worn, the reflected wave is generated at the second portion. Accordingly, the pulse wave detected by the first pressing bag 18 worn on the first portion of the upper arm 14 that is on the upstream side of the second pressing bag 20 in the direction of the blood flow in the artery is a composite wave consisting of the incident wave that represents an increase of the pressure of the artery resulting from ejection of blood from the left ventricle of the heart, and the reflected wave generated at the second portion of the upper arm 14 on which the second pressing bag 20 is worn. Since the magnitude and velocity of the reflected wave increase with an increase of the hardness of the artery, the time difference $\Delta T$ and the magnitude ratio R calculated by the arteriosclerosis-related information obtaining means 78 (SB9 through SB12) vary depending upon the degree of arteriosclerosis. Accordingly, the degree of arteriosclerosis can be evaluated based on the time difference $\Delta T$ and/or the magnitude ratio R calculated as described above. In the present apparatus 10, therefore, the degree of arteriosclerosis can be evaluated by attaching, to the subject, the cuff 12 including the first pressing bag 18 and the second pressing bag 20, without using an expensive apparatus. Further, the degree of arteriosclerosis can be evaluated more easily in the present apparatus 10 than in a conventional arrangement in which two detecting devices for detecting respective two heartbeat-synchronous signals are worn on a subject for evaluation of the degree of arteriosclerosis.

In the illustrated apparatus 10, the first pressing bag 18 and the second pressing bag 20 are connected integrally to each other by the belt-like bag 16 such that the first and second pressing bags 18, 20 are spaced from each other. Accordingly, the present apparatus 10 can be easily worn on the subject.

The illustrated apparatus 10 includes the first pressure changing means 70 which changes the pressure in the first pressing bag 18, and the blood-pressure determining means 72 which determines the blood pressure BP of the subject, based on the signal obtained from the first pressing bag 18 while the pressure in the first pressing bag 18 is changed by the first pressure changing means 70. According to this arrangement, in addition to the arteriosclerosis-related information, the blood pressure BP of the subject can be determined based on the signal obtained from the first pressing bag 18.

While the present invention has been described in detail in its presently preferred embodiment, by reference to the drawings, the invention may otherwise be embodied.

In the illustrated apparatus 10, the cuff 12 is worn on the upper arm 14 of the subject. The cuff 12 may be worn on a different portion, such as a femoral portion or an ankle of the subject.

In the illustrated apparatus 10, the first pressing bag 18 is used as the pulse-wave detecting device. As the pulse-wave detecting device, there may be employed an electronic pressure sensor that is adapted to be pressed on a living subject with a prescribed pressing force. The electronic pressure sensor is, for instance, of a semiconductor piezoresistance type, a semiconductor capacitance type, or a thin-film type.

In the illustrated apparatus 10, the pressure in the second pressing bag 20, i.e., the second pressing pressure PC2 is so controlled as to completely stop the flow of blood at the second portion of the upper arm 14 on which the second pressing bag 20 is worn. In view of a fact that a reflected wave is generated by restricting the blood flow to some degree, the second pressing pressure PC2 may be controlled to a value lower than the blood-flow stopping pressure employed in the illustrated embodiment, as long as the blood flow is restricted to some degree.

In the illustrated apparatus 10, the first pressing bag 18 functioning as the pulse-wave detecting device and the second pressing bag 20 functioning as the pressing device are connected integrally to each other by the belt-like bag 16. The first pressing bag 18 and the second pressing bag 20 may be worn on the subject separately from each other. For instance, a cuff that is generally used in a blood pressure measurement and includes a pressing bag may be worn on an upper arm of a subject as the pulse-wave detecting device while the pressing device may be worn on a distal side of the cuff, e.g., on a wrist. Even where the pulse-wave detecting device and the pressing device are worn on the subject separately from each other as described above, the pressing device can be worn on the subject without taking account of a problem of noise, since the pressing device is not used to detect a pulse wave. Thus, the pressing device can be easily attached to the subject, as compared with the case where the two detecting devices for detecting the two heartbeat-synchronous signals are worn on a subject for measuring a pulse-wave propagation velocity.

In the illustrated apparatus 10, the second pressing bag 20 is used as the pressing device and the pressure in the second pressing bag 20, i.e., the second pressing pressure PC2 can be changed by the second pressure changing means 74. As explained above, the second pressing pressure PC2 may be so controlled as to restrict the blood flow without completely stopping the blood flow. Accordingly, a rubber hose or a rubber band may be used as the pressing device.

In the illustrated apparatus 10, the pulse waves used for obtaining the arteriosclerosis-related information are detected after the blood pressure values BP have been determined. The pulse waves may be detected before the blood pressure values BP are determined. In this case, since the pulse-wave detecting pressure PM2 cannot be determined based on the blood pressure values BP, the pulse-wave detecting pressure PM2 may be a prescribed constant value. Alternatively, the pulse-wave detecting pressure PM2 may be determined as a pressure value that corresponds to a time point at which the magnitude of the pulse wave reaches a maximum during changing of the pressure in the first pressing bag 18 (the first pressing pressure PC1) under the control of the first pressure changing means 70.

In the illustrated apparatus 10, the pulse-wave detecting pressure PM2 is determined as the average value of the mean blood pressure $BP_{MEAN}$ and the diastolic blood pressure $BP_{DIA}$. The pulse-wave detecting pressure PM2 may be so determined as to be a value slightly smaller than the diastolic blood pressure $BP_{DIA}$, e.g., a value obtained by subtracting, from the diastolic blood pressure $BP_{DIA}$, a value α pre-set at 10 mmHg to 20 mmHg.

In the illustrated apparatus 10, the time of occurrence of the incident-wave component of the pulse of the blood-flow-stop brachial pulse wave is determined based on the peak point of the pulse of the brachial pulse wave detected when the second portion of the upper arm 14 on which the second pressing bag 20 is worn is not pressed by the second pressing bag 20. The time of occurrence of the incident-wave component of the pulse of the blood-flow-stop brachial pulse wave may be determined, for instance, based on the first inflection point, or the first local maximum point, of the pulse of the blood-flow-stop brachial pulse wave, that occurs subsequent to the rising point of the pulse.

In the illustrated apparatus 10, the time difference ΔT and the magnitude ratio R described above are obtained as the arteriosclerosis-related information. Either one of the time difference ΔT and the magnitude ratio R may be obtained as the arteriosclerosis-related information. In place of, or in addition to, the time difference ΔT and the magnitude ratio R, there may be used, as the arteriosclerosis-related information, a difference between the magnitude b of the pulse of the blood-flow-stop brachial pulse wave at the time of occurrence of the peak point of the reflected-wave component thereof and the magnitude a of the pulse of the blood-flow-stop brachial pulse wave at the time of occurrence of the peak point of the reflected-wave component thereof. Further, a ratio of the above-indicated difference to a pulse pressure PP of the pulse of the blood-flow-stop brachial pulse wave may be obtained as the arteriosclerosis-related information.

It is to be understood that the present invention may be embodied with other changes, improvements and modifications that may occur to one skilled in the art without departing from the spirit and scope of the invention.

What is claimed is:

1. An apparatus for evaluating a degree of arteriosclerosis of a living subject, comprising:

a pulse-wave detecting device adapted to be worn on a first portion of the living subject having a first pressing bag adapted to be wound around the first portion of the subject and a second pressing bag adapted to be worn on a second portion of the subject located on a distal side of the first portion, the first and second pressing bags being connected integrally to each other by a connecting member such that the first and second pressing bags are spaced apart from each other;

a pressing device adapted to be worn on the second portion of the subject, for pressing the second portion so as to stop a flow of blood at the second portion; and an arteriosclerosis-related information obtaining means for obtaining arteriosclerosis-related information used for evaluating said degree of arteriosclerosis of the subject, based on a peak point of an incident-wave component, and a peak point of a reflected-wave component, of a pulse of a pulse wave that is detected by the pulse-wave detecting device in a state in which the flow of blood is stopped by the pressing device.

2. An apparatus according to claim 1, wherein the arteriosclerosis-related information obtaining means obtains, as the arteriosclerosis-related information, a time difference between a time of occurrence of the peak point of the incident-wave component of the pulse and a time of occurrence of the peak point of the reflected-wave component of the pulse.

3. An apparatus according to claim 1, wherein the arteriosclerosis-related information obtaining means obtains, as the arteriosclerosis-related information, a difference between a magnitude of the pulse at a time of occurrence of the peak point of the incident-wave component thereof and a magnitude of the pulse at a time of occurrence of the peak point of the reflected-wave component thereof.

4. An apparatus according to claim 1, wherein the arteriosclerosis-related information obtaining means obtains, as the arteriosclerosis-related information, a ratio between a magnitude of the pulse at a time of occurrence of the peak point of the reflected-wave component thereof, and a magnitude of the pulse at a time of occurrence of the peak point of the incident-wave component thereof.

5. An apparatus according to claim 1, wherein the arteriosclerosis-related information obtaining means obtains, as the arteriosclerosis-related information, a ratio of a difference between a magnitude of the pulse at a time of occurrence of the peak point of the incident-wave component thereof and a magnitude of the pulse at a time of occurrence of the peak point of the reflected-wave component thereof, to a pulse pressure of the pulse of the pulse.

6. An apparatus according to claim 1, wherein the arteriosclerosis-related information obtaining means obtains, as the arteriosclerosis-related information, a ratio of a ratio between a magnitude of the pulse at a time of occurrence of the peak point of the incident-wave component thereof and a magnitude of the pulse at a time of occurrence of the peak point of the reflected-wave; component thereof, to a pulse pressure of the pulse.

7. An apparatus according to claim 1, wherein the pulse-wave detecting device comprises a pressing bag adapted to be wound around the first portion of the subject, and the apparatus further comprises: a pressure changing means for changing a pressure in the pressing bag; and a blood-pressure determining means for determining a blood pressure value of the subject based on a signal which is obtained from the pressing bag when the pressure in the pressing bag is changed by the pressure changing means.

8. An apparatus according to claim 1, further comprising: a first pressure changing means for changing a pressure in the first pressing bag; and a blood-pressure determining means for determining a blood pressure value of the subject based on a signal which is obtained from the first pressing bag when the pressure in the first pressing bag is changed by the first pressure changing means.

9. An apparatus according to claim 1, further comprising a second pressure changing means for changing a pressure in the second pressing bag.

10. An apparatus for evaluating a degree of arteriosclerosis of a living subject, comprising:

a pulse-wave detecting device adapted to be worn on a first portion of the living subject;

a pressing device adapted to be worn on a second portion of the subject located on a distal side of the first portion, for pressing the second portion so as to restrict a flow of blood at the second portion;

an arteriosclerosis-related information obtaining means for obtaining arteriosclerosis-related information used for evaluating said degree of arteriosclerosis of the subject, based on a peak point of an incident-wave component, and a peak point of a reflected-wave component, of a pulse of pulse wave that is detected by the pulse-wave detecting device in a state in which the flow of blood is restricted by the pressing device; and an incident-wave peak-point determining means for determining a time of occurrence of a peak point of an incident-wave component of a pulse of a pulse wave that is detected by the pulse-wave detecting device in a state in which the flow of blood is not restricted at the second portion by the pressing device.

11. An apparatus according to claim 10, wherein the arteriosclerosis-related information obtaining means determines the time of occurrence of the peak point of the incident-wave component determined by the incident-wave peak-point determining means, as a time of occurrence of the peak point of the incident-wave component of the pulse of the pulse wave that is detected in the state in which the flow of blood is restricted by the pressing device.

12. An apparatus for evaluating a degree of arteriosclerosis of a living subject, comprising:

a pulse-wave detecting device adapted to be worn on a first portion of the living subject having a first pressing bag adapted to be wound around the first portion of the subject and a second pressing bag adapted to be worn on a second portion of the subject located on a distal side of the first portion, the first and second pressing bags being connected integrally to each other by a connecting member such that the first and second pressing bags are spaced apart from each other;

a pressing device adapted to be worn on the second portion of the subject, for pressing the second portion so as to stop a flow of blood at the second portion; and an arteriosclerosis-related information obtaining device which obtains arteriosclerosis-related information used for evaluating said degree of arteriosclerosis of the subject, based on a peak point of an incident-wave component, and a peak point of a reflected-wave component, of a pulse of a pulse wave that is detected by the pulse-wave detecting device in a state in which the flow of blood is stopped by the pressing device.

* * * * *